US011607183B2

(12) United States Patent
Kim et al.

(10) Patent No.: US 11,607,183 B2
(45) Date of Patent: *Mar. 21, 2023

(54) AUTOMATED METHOD OF MANUFACTURING ORAL APPLIANCES

(71) Applicant: PROSOMNUS SLEEP TECHNOLOGIES, INC., Pleasanton, CA (US)

(72) Inventors: Sung Kim, Pleasanton, CA (US); David W. Kuhns, Pleasanton, CA (US); Leonard A. Liptak, Pleasanton, CA (US)

(73) Assignee: PROSOMNUS SLEEP TECHNOLOGIES, INC., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/374,587

(22) Filed: Jul. 13, 2021

(65) Prior Publication Data

US 2022/0071574 A1 Mar. 10, 2022

Related U.S. Application Data

(63) Continuation of application No. 16/285,113, filed on Feb. 25, 2019, now abandoned, which is a
(Continued)

(51) Int. Cl.
*G05B 19/4097* (2006.01)
*A61B 6/03* (2006.01)
(Continued)

(52) U.S. Cl.
CPC .............. *A61B 6/032* (2013.01); *A61B 1/24* (2013.01); *A61B 6/14* (2013.01); *A61B 34/10* (2016.02);
(Continued)

(58) Field of Classification Search
None
See application file for complete search history.

(56) References Cited

U.S. PATENT DOCUMENTS 9,155,599 B2 * 10/2015 Thompson ......... A61C 13/0004
9,808,327 B1 11/2017 Kim et al.
(Continued)

FOREIGN PATENT DOCUMENTS

| EP | 3487444 A1 | 5/2019 |
|---|---|---|
| WO | 2016046308 A1 | 3/2016 |
| WO | 2018017500 A1 | 1/2018 |

OTHER PUBLICATIONS

International Search Report and Written Opinion issued in PCT/US2017/042456 dated Aug. 10, 2017.
(Continued)

*Primary Examiner* — Jason Lin
(74) *Attorney, Agent, or Firm* — Greer, Burns & Crain Ltd.; Gregory P. Einhorn

(57) ABSTRACT

Disclosed herein are methods of manufacturing an oral appliance, the method comprising the steps of: a) importing into a computer aided design (CAD) computer program a digitized data set obtained from a three-dimensional scan of a patient's dentition; b) preparing a three-dimensional electronic model of the patient's dentition; c) subtracting the three-dimensional electronic model of the patient's dentition from an image of a solid block to obtain an appliance data set; and d) manufacturing a dental appliance in accordance with the appliance data set. Also disclosed are devices made by the above method, and methods of treating a condition, for example a sleep breathing disorder, by using a device made by the above method.

19 Claims, 1 Drawing Sheet

Related U.S. Application Data continuation of application No. 15/789,582, filed on Oct. 20, 2017, now Pat. No. 10,213,280, which is a continuation of application No. 15/416,715, filed on Jan. 26, 2017, now Pat. No. 9,808,327.

(60) Provisional application No. 62/365,974, filed on Jul. 22, 2016.

(51) Int. Cl.

| | | |
|---|---|---|
| *G16H 50/50* | (2018.01) | |
| *A61C 7/00* | (2006.01) | |
| *A61B 34/10* | (2016.01) | |
| *A61B 1/24* | (2006.01) | |
| *A61B 6/14* | (2006.01) | |
| *A61C 9/00* | (2006.01) | |
| *A61C 13/00* | (2006.01) | |
| *A61F 5/56* | (2006.01) | |
| *G16H 30/20* | (2018.01) | |

(52) U.S. Cl.
CPC ............ *A61C 7/002* (2013.01); *A61C 9/0046* (2013.01); *A61C 13/0004* (2013.01); *A61C 13/0006* (2013.01); *A61C 13/0019* (2013.01); *A61F 5/566* (2013.01); *G05B 19/4097* (2013.01); *G16H 30/20* (2018.01); *G16H 50/50* (2018.01); *A61B 2034/105* (2016.02); *A61B 2034/108* (2016.02); *A61F 2005/563* (2013.01)

(56) References Cited

U.S. PATENT DOCUMENTS

| | | | | |
|---|---|---|---|---|
| 9,820,882 | B2* | 11/2017 | Liptak | A61F 5/566 |
| 10,213,280 | B2 | 2/2019 | Kim et al. | |
| 2001/0002310 | A1* | 5/2001 | Chishti | A61B 6/466 |
| | | | | 433/213 |
| 2008/0286712 | A1* | 11/2008 | Imgrund | A61C 7/00 |
| | | | | 433/24 |
| 2009/0017410 | A1* | 1/2009 | Raby | A61C 7/146 |
| | | | | 433/2 |
| 2010/0018228 | A1 | 1/2010 | Flammang et al. | |
| 2014/0277665 | A1* | 9/2014 | Fisker | G06F 30/00 |
| | | | | 700/98 |
| 2015/0024345 | A1* | 1/2015 | Eftekhar Ashtiani | ........ |
| | | | | A61C 13/0022 |
| | | | | 428/542.8 |
| 2015/0238345 | A1* | 8/2015 | Decker | A61C 5/007 |
| | | | | 382/128 |
| 2015/0245890 | A1* | 9/2015 | Wouters | A61C 9/004 |
| | | | | 700/98 |
| 2016/0184129 | A1* | 6/2016 | Liptak | A61C 7/08 |
| | | | | 128/848 |
| 2016/0270886 | A1* | 9/2016 | Schulter | A61K 6/84 |
| 2017/0273763 | A1* | 9/2017 | Fisker | A61C 9/0046 |

OTHER PUBLICATIONS

International Preliminary Report on Patentability issued in PCT/US2017/042456 dated Jan. 22, 2019.

Non-Final Office Action issued by the USPTO in U.S. Appl. No. 15/416,715 dated Jun. 29, 2017.

Response to Non-Final Office Action issued in U.S. Appl. No. 15/416,715 dated Jul. 14, 2017.

Notice of Allowance issued by the USPTO in U.S. Appl. No. 15/416,715 dated Sep. 13, 2017.

Non-Final Office Action issued by the USPTO in U.S. Appl. No. 15/789,582 dated Apr. 30, 2018.

Response to Non-Final Office Action issued in U.S. Appl. No. 15/789,582 dated Jun. 30, 2018.

Notice of Allowance issued by the USPTO in U.S. Appl. No. 15/789,582 dated Oct. 17, 2018.

Extended European Search Report and Written Opinion issued in EP 17831644 dated Feb. 4, 2020—8 pages.

* cited by examiner

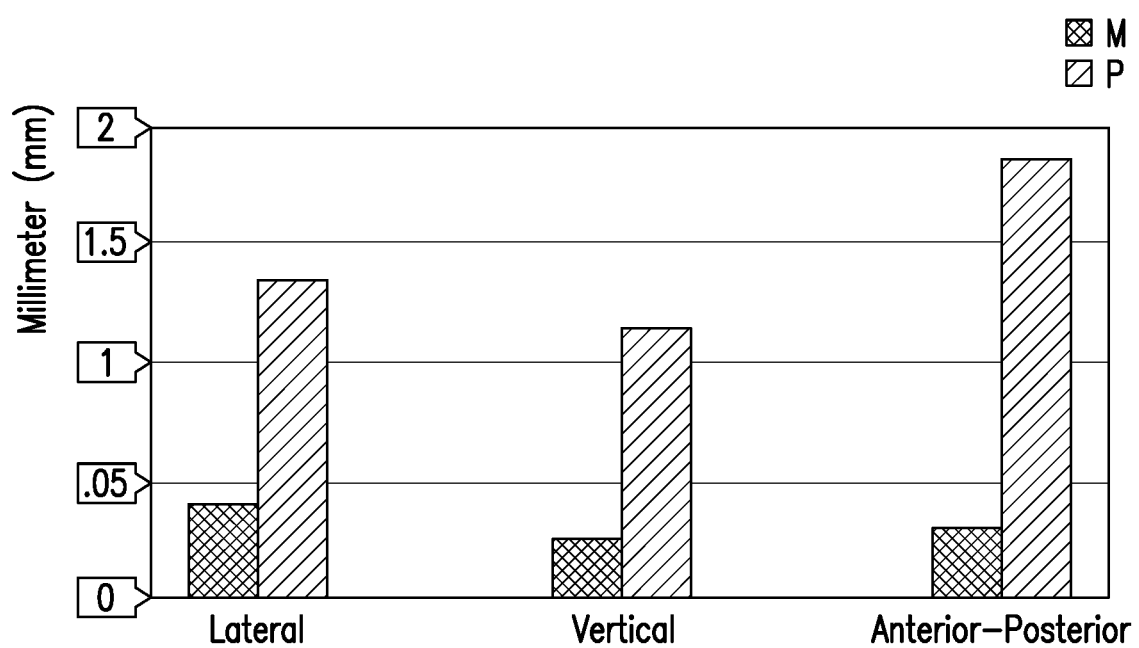

AUTOMATED METHOD OF MANUFACTURING ORAL APPLIANCES

RELATED APPLICATIONS

The present application is a continuation of U.S. patent application Ser. No. 16/285,113, filed Feb. 25, 2019, which is a continuation of U.S. patent application Ser. No. 15/789,582, filed Oct. 20, 2017, now U.S. Pat. No. 10,213,280, which is a continuation of U.S. patent application Ser. No. 15/416,715, filed Jan. 26, 2017, which claims priority to U.S. Provisional Application Ser. No. 62/365,974, filed Jul. 22, 2016, the entire disclosure of each of which is incorporated by reference herein.

FIELD OF THE INVENTION

This invention is in the field of digitized design and manufacture of an oral appliance.

BACKGROUND OF THE DISCLOSURE

Oral appliances, such as mandibular advancement devices, bruxing packages, AM positioners, and the like, are hand crafted to fit a plaster model of a patient's dentition. This process is laborious, leading to its high cost and inescapable variations from one device to another made by the same craftsperson, or from one craftsperson to another. If the initial device does not fit the patient well, or if the accessories are incorrectly placed, then the craftsperson must make a new device by hand crafting it from what is typically referred to as the "salt and pepper" method. This has a technician mixing the monomer of acrylate with the polymer of acrylate in a build-up process to create the oral appliance from scratch. The technician aligns, visually and with the aid of a ruler, the different components of the device, including the relative position of the titration mechanism to the patient's dentition and the relative position of bilateral components to each other, for example the placement of two jack screws situated at patient left and right.

The fit of the device on the dentition uses a classic process borrowed from the manufacture of dentures called "block out." Block out refers to the process of filling in the undercut of each tooth below the height of contour (see below for definition). The technician visually measures the amount of the undercut to block out to create just the right retention, not too much, not too little. A pencil or pen is used to draw a line along the height of contour and then blocking material such as dental putty is filled under that line.

The thickness of that pencil line is typically on the order of 0.5 mm to 1.0 mm and each technician may place that line in a different position. This cumulative error in defining dimensions is common in the dental laboratory and is very often accommodated for by the dentist with the patient in the chair by using a dental burr to adjust the appliance fit. Additionally, the cumulative error of the "salt and pepper" method and placement of the titration mechanism is accommodated for by the dentist, with the patient in the chair, by adjusting the titration mechanism, such as a jack screw. The adjustment repositions the relationship of the upper and lower splints to the desired position as requested by the dentist originally when submitting the patient data to the laboratory. It is a common practice that in case of a broken splint, an entire new upper and lower device needs to be made. Building a single splint to fit with an existing opposing splint is too difficult considering the accumulated errors in the process. In addition to being time-consuming, the inadvertent and inescapable variations between the original device and the new one introduce additional problems. For instance, in some applications where an exact positional difference between one feature of one splint and the corresponding feature of another splint cannot be properly determined because a handcrafted device exhibits inadvertent positional differences elsewhere that make the intended positional difference become a priori unmeasurable.

Medicare guidelines require an oral appliance for the treatment of obstructive sleep apnea (OSA) per the E0486 code, to have adjustments capability of 1.0 mm or less Clinical significance of titration adjustment has been shown by Almeida et. Al (reference) to be 0.5 mm or less. The challenge for dental and medical practitioners is to efficiently treat patients using small titration increments with oral appliances that have cumulative errors greater than what is clinically significant. Additionally, the cumulative error in all the x, y, and z axes can improperly position the appliance in the patient's mouth and affect the mandibular position as well. The repositioning can potentially lead to unwanted issues, or an exacerbation thereof, such as changes in the temporal mandibular joint (TMJ) or orthodontic tooth movements. Thus much time and treatment duration is wasted managing the appliance instead of managing the disease.

SUMMARY OF THE INVENTION

Disclosed herein are methods of manufacturing an oral appliance, the method comprising the steps of: a) preparing a three-dimensional electronic model of the patient's dentition; b) subtracting the three-dimensional electronic model of the patient's dentition from an image of a solid block to obtain an appliance data set; and c) manufacturing a dental appliance in accordance with the appliance data set. Also disclosed are methods of manufacturing an oral appliance, the method comprising the steps of: a) preparing a three-dimensional electronic model of the patient's dentition; b) design a "U" shaped surface covering the patient's dentition; c) adding walls, on either the lingual side, the buccal side, or both up to the contour curve; and d) adding the scalloped features of the patient's dentition. Also disclosed are devices made by the above methods, and methods of treating a condition, for example a sleep breathing disorder, by using a device made by the above method.

BRIEF DESCRIPTION OF THE DRAWINGS

FIG. 1 is a bar graph showing the differences between the patient measurement and the device measurement in the width along the x (Lateral) axis, the height along the y axis (Vertical), and the length along the z (Anterior-Posterior) axis of the lower splint.

DETAILED DESCRIPTION OF THE EMBODIMENTS

To overcome the problems enumerated above, among others, a method is developed to digitally design the desired oral appliance specific to an individual patient's dentition and clinical needs, and then manufacture the oral appliance using an automated manufacturing machine, such as, automated milling machine, 3-dimensional printers, laser ablation, or the like. By employing this approach, multiple oral appliances that are nearly identical in all respect, save for minor, designed adjustments, can be made. The appliances can be tested by the patient to see which appliance works best for treating the condition. Further, in some cases, as the patient's anatomy improves, readjustment of the appliance becomes necessary. However, replacement of an existing appliance can simply be manufactured from the stored digital file, whereas by traditional methods the patient is to be recalled in for new impressions. By employing the present methods, a new appliance can be made in which the adjustment is the only noticeable change in the fit from the previous appliance.

By "nearly identical" it is meant that the differences between the two appliances are within the tolerance of the manufacturing device, which tolerance is smaller than if the two appliances were manufactured by hand. In some embodiments, the measured difference between two appliances in any of the length, width, height, thickness, and distance between two points in an appliance is <0.5 mm, <0.1 mm, <0.05 mm, or <0.01 mm. In other embodiments, the difference between two appliances in any of the length, width, height, thickness, and distance between two points one appliance is <5%, <1%, <0.5%, or <0.1% of the measured values.

Herein, digitized design protocols that lead to manufacture of an oral appliance are presented.

In one aspect, disclosed herein are methods of manufacturing an oral appliance, the method comprising the steps of:
a) preparing a three-dimensional electronic model of the patient's dentition;
b) subtracting the three-dimensional electronic model of the patient's dentition from an image of a solid block to obtain an appliance data set; and
c) manufacturing a dental appliance in accordance with the appliance data set.

In some embodiments, the methods further comprise repeating steps a) through c) for the other of the patient's upper or lower dentition.

At the start of the process, a health care provider (HCP) examines the patient and obtains an impression of the patient's dentition, and models the bite by taking a bite impression in one or more positions of the mandible relative to maxilla. The impressions can be taken traditionally with dental impression material and poured up in stone either at the HCP office or at the manufacturing location (MFG).

In the context of the present discussion, the MFG is the location where the oral appliance is made. In some embodiments, this location is a facility outside of the HCP's office, for example, a third party manufacturing facility. In other embodiments, the HCP's office features a milling, or other manufacturing, devices that can manufacture the oral appliance. In these embodiments, the MFG is located within the HCP's office.

Obtaining the data regarding the shape of the patient's dentition is well-known to those of ordinary skill in the art. In some embodiments, the HCP obtains the dentition impression using trays filled with impression materials. The impression is then used to create a plaster model identical to the patient's dentition.

In some embodiments, the HCP provides photographs of the patient's dentition. A computerized three-dimensional image of the patient's dentition can then be prepared. In some embodiments, the patient's dentition is scanned directly, while in other embodiments, the plaster model of the patient's dentition is scanned. The scanning data is used to create a computerized three-dimensional image of the patient's dentition.

In some embodiments, the three-dimensional image of the patient's dentition is the image of the patient's bite when the patient is sleeping. In other embodiments, the patient's upper and lower dentitions are set in centric occlusion, while in other embodiments, the two dentitions are set in offset position to each other. The offset position is referred to as a "sleep bite" or "purposeful orthodontic protrusion."

The three-dimensional image is either obtained digitally, or is converted to a digital file. The digital file of the image is then imported into a computer aided design (CAD) software for designing the oral appliance.

In some embodiments, once the digitized image of the patient's dentition is obtained, the MFG provides the HCP with a completed image of the patient's bite, for example as a digitized image or a hardcopy print out, so that the HCP can determine if the bite is in the proper location. The HCP can, if necessary, make modifications on the image to the location of mandible with respect to maxilla. This adjustment would reflect, per the HCP's professional opinion, the best alignment for the patient's jaw for the treatment.

In some embodiments, the MFG incorporates within the CAD software standard designs for the oral appliance and any features or accessories (see below) that the HCP may have requested. These designs are general and basic, but can be modified, as discussed below, to match the particular needs of the individual patient.

The following steps in the disclosed methods comprise mathematical manipulations of a digital image for the oral appliance. Thus, when the disclosed methods require cutting out a certain section or thinning a certain part, it does not mean that an actual appliance was manipulated. Instead, it means that the digitized image of the appliance was mathematically manipulated within the CAD software.

In some embodiments, when the oral appliance comprises an upper jaw component and a lower jaw component, the components are designed independently and consecutively. In other embodiments, both components are designed simultaneously. Below, the design of the components is discussed separately. The skilled artisan realizes that the discussion below can be easily modified to design both components simultaneously. For ease of discussion, the process is first discussed in the context of preparing an oral appliance for the upper dentition. Of course, the skilled artisan realizes that the appliance for the lower dentition can be prepared first, or if the appliance is a single unit appliance, then the following process is used once for the single appliance.

In some embodiments, an image of a solid block is superimposed over the image of the patient's lower dentition. The solid block image follows the general contours of the desired oral appliance. For instance, if the desired oral appliance is a mandibular advancement splint, then the solid block has a basic (i.e., featureless) "U" shaped design, where the ends of the "U" fit over the molars and the curvature of the "U" fits over the incisors. Similarly, if the desired oral appliance is an AM positioner, then the solid block would have a basic rectangular block design. Other block shapes that resemble a well-known geometric shape, such as triangular, square, rhomboid, and the like, blocks, and blocks having a random shape are also contemplated.

In some embodiments, a Cartesian coordinate system is used to better define the position of the oral appliance. In some of these embodiments, the y axis is a part of the patient's sagittal plane, is parallel to the longitudinal axis, and points towards the roof of the patient's mouth and the head. The x and z axes are parts of the patient's transverse plane. The x axis is parallel to the medio-lateral axis and points buccally to the left. The z axis is parallel to the sagittal axis and points anteriorly.

The method steps below are discussed with reference to the design of an upper splint for the upper dentition. The skilled artisan realizes that identical methodology is used to design the lower splint for the lower dentition.

When the solid block is positioned over the dentition, the block has four different surfaces. The lower surface, i.e., a surface parallel to the transverse plane and away from the gingiva, is the "occlusal plane" of the appliance. The upper surface, parallel to the transverse plane and near the gingiva, is the "gingival plane." The curved plane in the interior of the "U," i.e., the plane near the tongue, is the "lingual plane," while the curved plane in the exterior of the "U," i.e., the plane near the cheek, is the "buccal plane."

In some embodiments, the gingival plane of the oral appliance is placed at the height of contour of one of the molars. "Height of contour" is a point visible to the eye on the buccal side of the molar, where the tooth is widest along the xz plane (e.g., where the tooth has the widest radius along the either the x or the z axis). In some embodiments, the molar is chosen arbitrarily. In certain embodiments, the molar is either the furthest posterior tooth, or the penultimate posterior tooth (e.g., any one of teeth 17-19 or 30-32). For the purposes of this discussion, the "height of contour" represents a point on the buccal side of the tooth.

In some embodiments, a "contour curve" is obtained by connecting the heights of contour of all the teeth, and then smoothing the curve such that the curve has a quasi-sinusoidal shape, i.e., it smoothly rises and drops as the height of contour of each tooth is located above or below the height of contour of the respective preceding tooth. In some embodiments, the contour curve is placed at an offset distance at the buccal side of the dentition, while in other embodiments, the contour curve is placed at an offset distance at the lingual side of the dentition. The offset distance is the distance between a tooth and the device in the xz, xy, and/or yz plane(s). The offset distance provides, inter alia, room for the oral appliance to be placed over the dentition, which placement generally follows along the y axis, without a fit that is too tight to cause discomfort for the patient. In some embodiments, the offset distance is a fraction of the visible buccal or lingual height of one of the posterior-most molars. The offset distance in step d) is between about 0% to about 100% of the tooth height. In certain embodiments, the offset distance is between about 20% to about 80% of the tooth height. In some embodiments, the offset distance is between about 0.01-about 0.5 mm. In other embodiments, the offset distance is between about 0.001-about 1.0 mm, while in other embodiments, the distance is greater than about 1.0 mm (e.g., about 1.1, about 1.3, about 1.5, about 1.7, about 1.9, or about 2.0 mm).

Throughout the present disclosure, the terms "up," "upper," or "upward," and "down," "lower," or "downward" refer to the relative position of the upper jaw and the lower jaw. Thus, "protruding downwardly" means protruding away from the upper jaw and towards the lower jaw. Accordingly, for the lower splint, "lower" means away from the occlusal plane and towards the gingiva, while "upper" means away from the gingiva and towards the occlusal plane. Likewise, for the upper splint, "lower" means away from the gingiva and towards the occlusal plane, while "upper" means away from the occlusal plane and towards the gingiva. Similarly, the words "front" or "forward" and "back" or "backward" refer to the relative position of components in the mouth. Thus, "front" means towards the lips (anteriorly), whereas "back" means towards the throat (posteriorly), when the device is in the mouth.

In some embodiments, the offset distance is the same as one moves around the device along the xz plane. In other embodiments, the offset distance varies as one moves around the device along the xz plane. In these embodiments, the offset distance is calculated for each single tooth or for a collection of few neighboring teeth. In some embodiments, the variance due to manufacturing limitations for the actual offset distance (i.e., the offset distance of the manufactured device) is <25%, <20%, <10%, <5%, or <1% of the calculated offset distance.

In some embodiments, the offset is tapered. In these embodiments, the offset is larger at the gingival plane of the device and gradually becomes smaller as one moves towards the occlusal plane. In these embodiments, as the patient places the device over the patient's dentition, the device moves over the dentition loosely at first, but the grip becomes tighter as the device is pressed further over the dentition. Additionally, in some embodiments the offset is tapered in the anterior-posterior direction, providing a variance in tightness for each tooth along the length of the upper or lower arch. In other embodiments, the offset is tapered in the occlusal-gingival direction. In some embodiments, the offset is specific for each tooth. In yet other embodiments, the HCP or the MFG designs and tapers the offset for a single targeted tooth. In some of these embodiments, the tooth-specific offset is then taken as a model for the offset tapering for other teeth. This variance may be customized to the patient's particular dentition or preference for comfort and fit.

By "about" a certain value it is meant that the stated value comprises the range of values within ±25%, ±20%, ±10%, or ±5% of the stated value. Thus, by way of example only, if a distance is given as "about 5 mm," the range of distances between 3.75 mm (5-25%) to 6.25 mm (5+25%) is envisioned.

In some embodiments, the contour curve is then moved along the y axis toward the gingival plane and away from the occlusal plane (i.e., the curve is moved "up"). If the gingival plane of the oral appliance is placed exactly at the contour curve, then the grip of the appliance on the dentition will be somewhat weak. However, if the contour curve is placed between the contour curve and the gingival plane, then the oral appliance will grip the dentition more strongly. The closer the contour curve is to the gingival plane, the stronger the grip. If the contour curve is too close to the gingival plane, then the patient will experience discomfort when the oral appliance is placed in the mouth or is removed from the mouth. In some cases, the grip will be too strong to remove the oral appliance, and can lead to the loosening of one or more of the teeth. Similarly, if the contour curve is placed too far from the gingival plane, then the oral appliance will be too loose during use and may inadvertently fall out. In some embodiments, the contour curve is moved towards the appliance's gingival plane by a distance that is a fraction of the visible buccal or lingual height of one of the posterior-most molars. In some embodiments, the fraction is between about 0% to about 100%, while in other embodiments, the fraction is between about 1% to about 50%, and in other embodiments, the fraction is between about 0.1% to about 90%.

In some embodiments, following the placement of the contour curve, the portion of the solid block between contour curve and the gingival surface is subtracted from the solid block to obtain a contour block. At this point, the gingival plane is no longer a 2-dimensional plane. The plane, now termed "gingival surface," is a curved surface whose curvature matches that of the contour curve.

Thus, in some embodiments, the lingual contour curve is moved "up" 100%, such that the appliance no longer has a lingual wall, while the buccal contour curve is moved "up"

by 20%, meaning that the buccal wall retains most of its original height. Similarly, in other embodiments, the buccal contour curve is moved up 100% while the lingual contour curve is moved up by 20%. In yet other embodiments, both lingual and buccal contour curves are moved up by a fraction <100%. In some of these embodiments, the two contour curves are moved by the same fraction, while in other embodiments, the two contour curves are moved by different fractions.

In some embodiments, the three-dimensional electronic model of the patient's dentition is subtracted from the contoured block to obtain an appliance data set. The data set is then communicated with a manufacturing device and an oral appliance is made in accordance with the appliance data set.

In some embodiments, the digitized data set is obtained from: i) scanning a model of the patient's dentition; ii) the patient's dentition directly; iii) X-ray image of the patient's dentition; iv) computed tomographic (CT) scan of the patient's dentition; v) magnetic resonance image (MRI) of the patient's dentition; or vi) digitized photographs of the patient's dentition.

In some embodiments, the digitized data set is created in the HCP's office, having direct contact with the patient, while in other embodiments, the digitized data set is created in the MFG.

In some embodiments, the methods described herein further comprise the step of mathematically including the image of an appliance accessory, or an appliance accessory connection point, to the appliance data set. In some embodiments, the image of the accessory or its connection point is added to the electronic image of the splint. In other embodiments, the image of the accessory or its connection point are subtracted from the original solid block. In some embodiments, the appliance accessory is selected from the group consisting of a compliance chip, an electronic or microelectronic device, a "smart" accessory (i.e., an electronic device that obtains data and communicates the data with another electronic device), strap, affixed sleeve, removable sleeve, straps, anterior hinge, short or long Herbst, jack screw, and Herbst hinge in combination with jack screw, or any other appliance accessory now known or designed in the future. In some embodiments, the accessory is a separate manufacture than the dental device. In these embodiments, the accessory itself is attached to the device after the manufacturing of the device. In other embodiments, the accessory is part of the unitary design of the device. In these embodiments, the accessory comes to being at the same time the device is manufactured.

In some embodiments, the methods described herein further comprise the step of mathematically including (by adding or subtracting) the image of an appliance design feature to the appliance data set. In some embodiments, the appliance design feature is selected from the group consisting of a fin, anterior opening, anterior discluder, scalloped occlusal opening, lingual opening, a tapered posterior, a tongue attractor, lingualess, full lingual coverage, edentulous, posterior lingual, anterior lingualess, and monoblock.

In some embodiments, the appliance design feature is pre-programmed into the CAD software. In certain embodiments, the MFG modifies or manipulates the pre-programmed design feature to create a unique design feature (i.e., shape, placement location, size, and the like) that meets the idiosyncratic needs of the patient.

In some embodiments, the appliance is manufactured additively, while in other embodiments, the appliance is manufactured subtractively. By "additive manufacturing" it is meant that the future device begins at a nucleus and grows from the nucleus. Examples of additive manufacturing include 3-dimensional printing (where the device grows out of a pool of monomers), injection molding (where the mold is filled with the monomer). By "subtractive manufacturing" it is meant that the future device is carved out of a block of material. Examples of subtractive manufacturing include hand carving and milling.

In some embodiments, the appliance is manufactured automatedly, while in other embodiments, the appliance is handcrafted. In certain embodiments, the appliance is manufactured by a method selected from the group consisting of milling a block, injection molding, three-dimensional printing, computer-aided manufacturing technology and hand carving.

In some embodiments, the appliance is manufactured by a combination of two or more subtractive manufacturing techniques, or by a combination of two or more additive manufacturing techniques, or by a combination of one or more subtractive manufacturing techniques and one or more additive manufacturing techniques.

In certain embodiments, the appliance is made of a material that is, inter alia, physiologically acceptable, has sufficient strength for the desired function but malleable enough to be conveniently placed over the dentition, and is not repugnant to the patient when placed in the mouth. In certain embodiments, the appliance is manufactured from a polymer, a composite, a thermoplastic, a thermoset, and the like. In some embodiments, the appliance is subtractively manufactured from a block of, or additively manufactured to form, a material selected from the group consisting of standard polymethylmethacrylate (PMMA), lined PMMA, high-strength polyetheretherketone (PEEK), polymer produced from polyoxymethylene and acetal copolymers (Duracetal®), glycol modified polyethylene terephthalate (PETg), and a physiologically compatible, water insoluble, non-malleable polymer, wood, and metal.

In one aspect, disclosed herein are methods of manufacturing an oral appliance, the method comprising the steps of:
  a) preparing a three-dimensional electronic model of the patient's dentition;
  b) superimposing an image of a solid block over the electronic model of one of the patient's upper or lower dentition,
      wherein the solid block has a "U" shape that approximates the curvature of the patient's dentition, and
      whereby the gingival surface of the solid block is at about the height of contour of a molar tooth of the dentition;
  c) determining the contour curve for the dentition, wherein the contour curve is placed at an offset distance at either the buccal or lingual side of the dentition, wherein the offset distance is between about 20% to about 80% of the visible tooth height of one of the posterior-most molars;
  d) moving the height of contour curve towards the gingival line by a distance of about between about 1% to about 50% of the visible tooth height of one of the posterior-most molars;
  e) subtracting the portion of the solid block below the height of contour curve to obtain a contoured block;
  f) subtracting the three-dimensional electronic model of the patient's dentition from the contoured block to obtain an appliance data set;
  g) automatedly manufacturing a dental appliance in accordance with the appliance data set.

The above methods describe a subtractive design methodology, where digitally the device is carved out of a solid block. It is also within the scope of the present disclosure that the design of the devices disclosed herein are carried out additively. In an additive design, the designer begins with an empty space and gradually adds features of the device until the device design is completed.

The features of the presently disclosed digital additive design include:
 a) preparing a three-dimensional electronic model of the patient's dentition;
 b) design a "U" shaped surface covering the patient's dentition;
 c) adding walls, on either the lingual side, the buccal side, or both up to the contour curve; and
 d) adding the scalloped features of the patient's dentition.

It is understood that some or all of the presently disclosed method steps are applicable to the additive design methods as well as the above-described subtractive design methods.

In some embodiments, the disclosed splints are designed by a combination of additive and subtractive methods (add/subtractively). For example, in some embodiments, the splint is designed subtractively while the inclusion of the accessories is designed additively. In other embodiments, the splint itself can be designed add/subtractively. In some of these embodiments, a feature (e.g., a lingual wall) is added, but then the feature is subtractively reduced until the desired feature is obtained (e.g., wall height is subtracted up to the contour curve).

In some embodiments, a feature, such as an extrusion, is designed in CAD. In other embodiments, the feature is a group of features that are designed and then merged together in CAD to make a desired and complete splint. In some embodiments, the designed feature comprises a standard and well-defined geometrical shape, for example a cube, a pyramid, a cone, a cylinder. A well-defined geometrical shape is one in which the cross section of the feature is a standard geometrical shape of a circle, a square, a rectangle, a parallelogram, a circle, a triangle, a rhombus, and the like. In other embodiments, the feature comprises a customized shape. The customized shape is one in which the cross section is a non-standard, or amorphous, geometrical shape. In some embodiments, the feature is entirely made up of one, or a merger of two or more, standard geometrical shapes. In other embodiments, the feature is entirely made up of one, or a merger of two or more, non-standard geometrical shapes. In other embodiments, the feature comprises between 10%, 20%, 30%, 40%, 50%, 60%, 70%, 80% or 90% of one or more standard geometrical shape(s), with the remainder being comprised of one or more non-standard shape(s).

In other embodiments, the feature (e.g., a tapered offset) is adjusted in an iterative process of addition and subtraction (for example at least two cycles of addition and subtraction) until an optimized design (e.g., a taper that fits the patient's dentition very well) is obtained. The artisan of ordinary skill understands that while the above processes are given an example for illustration, the design processes can be used with any feature of the splints or their accessories.

In another aspect, disclosed herein are oral appliances manufactured by the methods described above.

As discussed in the Background section, currently oral appliances are made by hand, which leads to appliances that are both poorly fit to the patient's dentition and have high enough variance in each aspect to render them irreproducible. By contrast, oral appliances manufactured by the presently disclosed methods have very low variances when they are manufactured.

To illustrate this point, a traditional oral appliance, i.e., one made by the current artisanal, hand-made, methods was ordered from a leading manufacturer for a patient. Another appliance was prepared by the methods disclosed herein for the same patient. The difference between the measurement provided to the manufacturer for a particular point on the device versus the measurement of the same point on the prepared device was determined. FIG. 1 illustrates the results. In the FIGURE, the dark shade bars show the results for the device manufactured by the present methods, designated "M," whereas the light shade bars show the results for the purchased device, designated "P."

The bars show the differences between the patient measurement and the device measurement in width along the x (Lateral) axis, the height along the y axis (Vertical), and the length along the z (Anterior-Posterior) axis of the lower splint. Along the x axis, the P device showed a difference of about 1.3 mm, whereas the M device showed a mere difference of about 0.4 mm, which was a 2.3 times greater accuracy for the M device. Similarly, along the y axis, the P device showed a difference of about 1.1 mm, whereas the M device showed a mere difference of about 0.2 mm, which was a 3.6 times greater accuracy for the M device. The differences for the z axis where even more drastic. The P device showed a difference of about 1.8 mm, whereas the M device showed a mere difference of about 0.3 mm, which was a 5.2 times greater accuracy for the M device.

In another aspect, disclosed herein are methods of treating or ameliorating a condition in a patient, the method comprising: identifying a patient in need thereof, obtaining an oral appliance manufactured by the methods described above, and positioning the oral appliance in the patient's mouth, such that the condition is treated or ameliorated.

In some embodiments, the condition is a sleep breathing disorder. In some embodiments, the condition is one in which the repositioning of the patient's dentition treats or ameliorates the condition. Examples of the conditions include, but are not limited to, sleep apnea, teeth grinding, and improperly positioned mandible.

What is claimed is:

1. A method of manufacturing an oral appliance, the method comprising the steps of:
 a) preparing a three-dimensional electronic model of a patient's dentition and generating a digitized data set;
 b) determining a contour curve for the dentition, wherein the contour curve is placed at an offset distance at either the buccal or lingual side of the dentition, and the offset distance is a fraction of a visible buccal or a lingual height of a posterior-most molar;
 c) subtracting the three-dimensional electronic model of the patient's dentition from an image of a solid block to obtain an appliance data set; and
 d) manufacturing a dental appliance in accordance with the appliance data set and the contour curve.

2. The method of claim 1, further comprising the step of superimposing the image of the solid block over one of an upper or a lower dentition of the patient prior to the subtracting step.

3. The method of claim 2, wherein the three-dimensional electronic model solid block is superimposed such that a gingival surface of the solid block is at a height of contour of a molar tooth of the dentition.

4. The method of claim 1, further comprising the step of moving the contour curve towards a gingival line by a distance that is a fraction of the visible buccal or lingual height of the posterior-most molar.

5. The method of claim 4, further comprising the step of subtracting a portion of the solid block below the contour curve to obtain a contoured block.

6. The method of claim 5, wherein the contoured block is the solid block used in the subtracting step.

7. The method of claim 4, wherein the contour curve is moved by between about 0 to about 100% of a tooth height.

8. The method of claim 1, wherein the solid block has a shape that approximates a shape of the oral appliance.

9. The method of claim 1, wherein steps b)-d) are first carried out for manufacturing an oral appliance for one of an upper or a lower dentition, and then steps b)-d) are repeated for manufacturing an oral appliance for the other of the patient's upper or lower dentition.

10. The method of claim 1, wherein the offset distance is between about 0 to about 100% of a tooth height.

11. The method of claim 1, wherein the digitized data set is obtained from:
   i) scanning a model of the patient's dentition;
   ii) the patient's dentition directly;
   iii) an X-ray image of the patient's dentition;
   iv) a computed tomographic (CT) scan of the patient's dentition; or
   v) a digitized photograph or photographs of the patient's dentition.

12. The method of claim 1, further comprising adding a digitized image of an appliance accessory, an appliance accessory connection point, or an appliance design feature to the digitized data set to generate a digitized appliance data set.

13. The method of claim 12, wherein the appliance accessory is selected from a group consisting of a fin, a strap, an affixed sleeve, a removable sleeve, a strap, an anterior hinge, a short or a long Herbst, a jack screw, and a Herbst hinge in combination with jack screw.

14. The method of claim 12, wherein the appliance design feature is selected from a group consisting of: an anterior opening, an anterior discluder, a scalloped occlusal opening, a lingual opening, a compliance chip, a tapered posterior, a tongue attractor, a lingualess, a full lingual coverage, an edentulous, posterior lingual, anterior lingualess, and monoblock.

15. The method of claim 1, wherein the manufacturing process comprises milling a block, injection molding, three-dimensional printing, computer aided manufacturing technology, hand carving or a combination thereof.

16. A method of manufacturing a splint for a dental appliance, the method comprising the steps of:
   a) preparing a three-dimensional electronic model of a patient's dentition;
   b) superimposing an image of a solid block over the three-dimensional electronic model of one of the patient's upper or lower dentition,
   wherein the solid block has a "U" shape that approximates a curvature of the patient's dentition, and
   whereby a gingival surface of the solid block is at about a height of contour of a molar tooth of the dentition;
   d) determining a contour curve for the dentition,
   wherein the contour curve is placed at an offset distance at either the buccal or lingual side of the dentition,
   wherein the offset distance is between about 20% to about 80% of a visible tooth height of one of a posterior-most molar;
   e) moving the height of contour curve towards a gingival line by a distance of about between about 1% to about 50% of the visible tooth height of the posterior-most molar;
   f) subtracting a portion of the solid block below the height of the contour curve to obtain a contoured block;
   g) subtracting the three-dimensional electronic model of the patient's dentition from the contoured block to obtain an appliance data set; and
   h) manufacturing the splint for the dental appliance in accordance with the appliance data set.

17. A method of manufacturing a dental appliance, the method comprising the steps of:
   a) preparing a three-dimensional electronic model of a patient's dentition;
   b) superimposing an image of a solid block over the three-dimensional electronic model of one of the patient's upper or lower dentition,
   wherein the solid block approximates a curvature of the patient's dentition, and
   whereby a gingival surface of the solid block is at about a height of contour of a molar tooth of the dentition;
   d) determining a contour curve for the dentition,
   wherein the contour curve is placed at an offset distance at either the buccal or lingual side of the dentition,
   wherein the offset distance is between about 20% to about 80% of a visible tooth height of one of a posterior molar;
   e) moving the height of contour curve towards a gingival line by a distance of about between about 1% to about 50% of the visible tooth height of the posterior molar;
   f) subtracting a portion of the solid block image below the height of the contour curve to obtain a contoured block image;
   g) subtracting the three-dimensional electronic model of the patient's dentition from the contoured block image to obtain an appliance data set; and
   h) manufacturing the dental appliance from the solid block in accordance with the appliance data set.

18. The method of claim 17, wherein the manufacturing comprises milling the solid block, injection molding, three-dimensional printing, computer aided manufacturing technology, hand carving or a combination thereof.

19. The method of claim 17, further comprising adding a digitized image of an appliance accessory, an appliance accessory connection point, or an appliance design feature to the appliance data set to generate a digitized appliance data set.

* * * * *